US008557962B2

(12) United States Patent
Stroes (10) Patent No.: US 8,557,962 B2
(45) Date of Patent: Oct. 15, 2013

(54) TREATMENT OF ENDOTHELIAL DYSFUNCTION IN DIABETIC PATIENTS

(75) Inventor: Erik S. G. Stroes, Amsterdam (NL)

(73) Assignee: CSL Limited, Parkville, Victoria (AU)

( * ) Notice: Subject to any disclaimer, the term of this patent is extended or adjusted under 35 U.S.C. 154(b) by 248 days.

(21) Appl. No.: 13/017,930

(22) Filed: Jan. 31, 2011

(65) Prior Publication Data
US 2011/0190193 A1 Aug. 4, 2011

Related U.S. Application Data

(63) Continuation of application No. 11/712,404, filed on Mar. 1, 2007, now Pat. No. 7,956,035.

(51) Int. Cl.
*A61K 38/17* (2006.01)
*A61P 9/00* (2006.01)

(52) U.S. Cl.
USPC .............................. 530/359; 514/1.1; 424/9.1

(58) Field of Classification Search
USPC ...................... 530/350, 359; 514/1.1; 424/9.1
See application file for complete search history.

(56) References Cited

U.S. PATENT DOCUMENTS

| 5,089,602 | A  | 2/1992 | Isliker et al. |
| 5,128,318 | A  | 7/1992 | Levine et al. |
| 5,652,339 | A  | 7/1997 | Lerch et al. |
| 7,053,049 | B2 | 5/2006 | Luescher et al. |
| 7,361,739 | B2 | 4/2008 | Bellotti et al. |
| 2005/0175666 | A1 | 8/2005 | Ding |
| 2006/0205643 | A1 | 9/2006 | Cuzzocra et al. |

FOREIGN PATENT DOCUMENTS

| WO | WO 01/13939 A1 | 3/2001 |
| WO | WO 01/38395 A1 | 5/2001 |
| WO | WO 2006/102395 A2 | 9/2006 |

OTHER PUBLICATIONS

Börü et al., "Prevalence of Peripheral Neuropathy in Type 2 Diabetic Patients Attending a Diabetes Center in Turkey," *Endocrine Journal*, vol. 51, No. 6, pp. 563-567, 2004.
Ba Ł a et al., "Characteristics of patients with type 2 diabetes of short duration in Poland," *Polskie Archiwum Medycyny Wewnetrznej*, vol. 119, No. 9, pp. 533-539, 2009.
Al-Wakeel et al., "Microvascular and Macrovascular Complications in Diabetic Nephropathy Patients Referred to Nephrology Clinic," *Saudi J. Kidney Dis. Transplant*, vol. 20, No. 1, pp. 77-85, 2009.
Liu et al., "Prevalence of chronic complications of type 2 diabetes mellitus in outpatients—a cross-sectional hospital based survey in urban China," *Healthy and Quality of Life Outcomes*, vol. 8, No. 62, 2010.
Ren et al., "Impact of Antioxidants and HDL on Glycated LDL-Induced Generation of Fibrinolytic Regulators From Vascular Endothelial Cells," *Arterioscler. Thromb. Vasc. Bio.*, vol. 20, pp. 1688-1693 (2000).
Newton et al., "HDL therapy for the acute treatment of atherosclerosis," *Atherosclerosis Supplements*, vol. 3, pp. 31-38 (2002).
Marchesi et al., "Therapeutic use of the high-density lipoprotein protein and peptides," *Expert Opin. Investig.: Drugs*, vol. 15, No. 3, pp. 227-241 (2006).
Newton, "HDL Therapy for the Sub-Acute Treatment of Patients with Acute Coronary Syndromes," *XIV International Symposium on Atherosclerosis*, Rome, Italy, Jun. 18-22, 2006.
Sirtori et al., "High Density Lipoprotein Administration: A New Therapeutic Modality for the Treatment of Cardiovascular Diseases," *Curr. Med. Chem.—Immun. Endoc. & Metab. Agents*, vol. 5, pp. 321-333 (2005).
Alp, N. J., et al., "Tetrahydrobiopterin-dependent preservation of nitric oxide-medicated endothelial function in diabetes by targeted transgenic GTP-cyclohydrolase I overexpression," The Journal of Clinical Investigation, 112(5): 725-735 (2003).
Balletshofer, B. M., et al., "Intense Cholesterol Lowering Therapy with a HMG-CoA Reductase Inhibitor does not Improve Nictric Oxide Dependent Endothelial Function in type-2 Diabetes A Multicenter, Randomised, Double-Blind, Three-Arm Placebo-Controlled Clinical Trial," Experimental and Clinical Endocrinology & Diabetes, 113: 324-330 (2005).
Bisoendial R. J., et al., "Consequences of Cholesteryl Ester Transfer Protein Inhibition in Patients With Familial Hypoalphalipoproteinemia," Arteriosclerosis, Thrombosis, and Vascular Biology, 25 : e133-e134, (2005), http://www.atvbaha.org.
Bisoendial, R. J., et al., "Restoration of Endothelial Function by Increasing High-Density Lipoprotein in Subjects With Isolated Low High-Density Lipoprotein," Circulation 107:2944-2948 (2003) http://circ.ahajournals.org.
Brousseau, M. E., et al., "Effects of an Inhibitor of Cholesteryl Ester Transfer Protein on HDL Cholesterol," The New England Journal of Medicine 350:1505-1515 (2004).
Brownlee, M., "Biochemistry and molecular cell biology of diabetic complications," Nature 414:813-820 (Dec. 2001).
Cheung, B. M. Y., et al., "Meta-analysis of large randomized controlled trials to evaluate the impact of statins on cardiovascular outcomes," British Journal of Clinical Pharmacology 57(5):640-651 (2003).
Cockerill, G. W., et al., "High-Density Lipoprotein: Multipotent Effects on Cells of the Vasculature," International Review of Cytology 188:257-297 (1999).

(Continued)

*Primary Examiner* — Chih-Min Kam
(74) *Attorney, Agent, or Firm* — Foley & Lardner LLP (57) ABSTRACT

A method for the treatment of endothelial dysfunction in a diabetic patient, including both diabetes induced macrovascular disorders and diabetes induced microvascular disorders, comprises administration, preferably parenteral administration, to the patient of an effective amount of high density lipoprotein (HDL).

16 Claims, 3 Drawing Sheets

(56) References Cited

OTHER PUBLICATIONS

Colhoun, H. M., et al., "Primary prevention of cardiovascular disease with atorvastatin in type 2 diabetes in the Collaborative Atorvastatin Diabetes Study (CARDS): multicentre randomised placebo-controlled trial," Lancet 364:685-696 (2004).

Dimayuga, P., et al., "Reconstituted HDL Containing Human Apolipoprotein A-1 Reduces VCAM-1 Expression and Neointima Formation Following Periadventitial Cuff-Induced Carotid Injury in apoE Null Mice," Biochemical and Biophysical Research Communications 264:465-468 (1999).

Du, X., et al., "Insulin resistance reduces arterial prostacyclin synthase and eNOS activities by increasing endothelial fatty acid oxidation," The Journal of Clinical Investigation 116(4): 1071-1080 (Apr. 2006).

Gordon, D. J., et al., "High-Density Lipoprotein Cholesterol and Cardiovascular Disease Four Prospective American Studies," Circulation 79:8-15 (1989).

Govers, R. et al., "Cellular regulation of endothelial nitric oxide synthase," Am J. Physiol Renal Physiol 280: F193-F206 (2001).

Haffner, S. M., MD, "Coronary Heart Disease in Patients With Diabetes," The New England Journal of Medicine, 342(14):1040-1042 (Apr. 6, 2000).

Hedrick C. C., et al., "Glycation impairs high-density lipoprotein function," Diabetologia, 43:312-320 (2000).

Heitzer, T., et al., "Tetrahydrobiopterin improves endothelium-dependent vasodilation by increasing nitric oxide activity in patients with Type II diabetes mellitus," Diabetologia 43:1435-1438 (2000).

Keech, A., et al., "Effects of long-term fenofibrate therapy on cardiovascular events in 9795 people with type 2 diabetes mellitus (the FIELD study): randomised controlled trial," Lancet 366:1849-1861 (2005).

Lerch, P. G., et al., "Production and Characterization of a Reconstituted High Density Lipoprotein for Therapeutic Applications," Vox Sang 71:155-164 (1996).

Lerch, P. G., et al., "Reconstituted High Density Lipoprotein (rHDL) Modulates Platelet Activity In Vitro and Ex Vivo," Thromb Haemost 80:316-320 (1998).

Matsunaga, T., et al., "Glycated High-Density Lipoprotein Regulates Reactive Oxygen Species and Reactive Nitrogen Species in Endothelial Cells," Metabolism 52(1):42-49 (Jan. 2003).

Matz, C. E., et al., "Micellar Complexes of Human Apolipoprotein A-I with Phosphatidylcholines and Cholesterol Prepared from Cholate-Lipid Dispersions," The Journal of Biological Chemistry 257(8):4535-4540 (Apr. 25, 1982).

Mineo, C., et al., "Endothelial and Antithrombotic Actions of HDL," Circ Res, 98:1352-1364 (2006).

Mineo, C., et al., "High Density Lipoprotein-induced Endothelial Nitric-oxide Synthase Activation Is Mediated by Akt and MAP Kinases," The Journal of Biological Chemistry, 278(11):9142-9149 (Mar. 14, 2003).

Moudry, R., et al., "Reconstituted High Density Lipoprotein Modulates Adherence of Polymorphonuclear Leukocytes to Human Endothelial Cells," SHOCK, 7(3):175-181 (1997).

Nanjee, M. N., et al., "Acute Effects of Intravenous Infusion of ApoA1/Phosphatidylcholine Discs on Plasma Lipoproteins in Humans," Arteriosclerosis, Thrombosis, and Vascular Biology 19:979-989 (1999).

Nissen, S. E., et al., "Effect of Recombinant ApoA-I Milano on Coronary Atherosclerosis in Patients With Acute Coronary Syndromes: A Randomized Controlled Trial," JAMA 290(17): 2292-2300 (2003).

Nobécourt, E., et al., "Defective antioxidative activity of small dense HDL3 particles in type 2 diabetes: relationship to elevated oxidative stress and hyperglycaemia," Diabetologia 48:529-538 (2005).

Pászty, C., et al., "Apolipoprotein Al Transgene Corrects Apolipoprotein E. Deficiency-induced Atherosclerosis in Mice," The Journal of Clinical Investigation 94:899-903 (1994).

Pyörälä, K., MD, et al., "Cholesterol Lowering With Simvastatin Improves Prognosis of Diabetic Patients With Coronary Heart Disease," Diabetes Care 20(4):614-620 (Apr. 1997).

Rohrer, L., et al., "High density lipoproteins in the intersection of diabetes mellitus, inflammation and cardiovascular disease," Current Opinion in Lipidology 15:269-278 (2004).

Schächinger, V., et al., "Prognostic Impact of Coronary Vasodilator Dysfunction on Adverse Long-Term Outcome of Coronary Heart Disease," Circulation, 101:1899-1906 (2000).

Spieker, L. E., et al., "High-Density Lipoprotein Restores Endothelian Function in Hypercholesterolemic Men," Circulation 105:1399-1402 (2002).

Stroes, E. S. G., et al., "Vascular function in the forearm of hypercholesterolaemic patients off and on lipid-lowering medication," Lancet 346:467-471 (1995).

Stroes, E., et al., "Tetrahydrobiopterin Restores Endothelial Function in Hypercholesterolemia," The Journal of Clinical Investigation 99(1):41-46 (1997).

Takano, S., PhD., et al., "Dual Roles of 5-Hydroxytryptamine in Ischemia-Reperfusion Injury in Isolated Rat Hearts," J. Cardiovasc Pharmacol Therapeut 9(1):43-50 (2004).

Tangirala, R. K., et al., "Regression of Artherosclerosis Induced by Liver-Directed Gene Transfer of Apolipoprotein A-I in Mice," Circulation 100:1816-1822 (1999).

Ting, H. H., et al., "Vitamin C Improves Endothelium-dependent Vasodilation in Patients with Non-Insulin-dependent Diabetes Mellitus," J. Clinical Investigation 97(1):22-28 (1996).

Tsutsumi, K, et al., "The Novel Compound NO-1886 Increases Lipoprotein Lipase Activity With Resulting Elevation of High Density Lipoprotein Cholesterol, and Long-Term Administration Inhibits Atherogenesis in the Coronary Arteries of Rats With Experimental Atherosclerosis," The Journal of Clinical Investigation 92:411-417 (1993).

Turner, R. C., et al., "Risk factors for coronary artery disease in non-insulin dependent diabetes mellitus: United Kingdom prospective diabetes study (UKPDS: 23)," BMJ 316:823-828 (1998).

Van Etten R. W., et al., "Impaired NO-dependent vasodilation in patients with Type II (non-insulin-dependent) diabetes mellitus is restored by acute administration of folate," Diabetologia 45:1004-1010 (2002).

Van Etten, R. W., et al., "Intensive Lipid Lowering by Statin Therapy Does Not Improve Vasoreactivity in Patients With Type 2 Diabetes," Arteriosclerosis, Thrombosis, and Vascular Biology 22:799-804 (2002).

Woodman, R. J., et al., "Basal production of nitric oxide (NO) and non-NO vasodilators in the forearm microcirculation in Type 2 diabetes: Associations with blood pressure and HDL cholesterol," Diabetes Research and Clinical Practice 71:59-67 (2006).

Yuhanna, I. S., et al., "High-density lipoprotein binding to scavenger receptor-BI activates endothelial nitric oxide synthase," Nature Medicine 7(7):853-857 (2001).

Nieuwdorp et al., "Restoration of Endothelial Function After Infusion of Reconstituted High-Density Lipoprotein in Subjects with Type 2 Diabetes Mellitus," *Circulation*, vol. 114, No. 18, Suppl. S. p. 255, Oct. 31, 2006.

Office Action issued on Jun. 15, 2010 by the Examiner in U.S. Appl. No. 11/712,404 (US 2008/0214434).

Office Action issued on Jan. 28, 2010 by the Examiner in U.S. Appl. No. 11/712,404 (US 2008/0214434).

Office Action issued on May 18, 2009 by the Examiner in U.S. Appl. No. 11/712,404 (US 2008/0214434).

Office Action issued on Aug. 28, 2008 by the Examiner in U.S. Appl. No. 11/712,404 (US 2008/0214434).

Office Action issued on Apr. 4, 2008 by the Examiner in U.S. Appl. No. 11/712,404 (US 2008/0214434).

TREATMENT OF ENDOTHELIAL DYSFUNCTION IN DIABETIC PATIENTS

FIELD OF INVENTION

This invention relates to a method for the treatment of endothelial dysfunction in diabetic patients. In particular, this invention relates to a method for improving endothelial function in treatment of disorders which are related to endothelial dysfunction, both macrovascular and microvascular, in diabetic patients.

BACKGROUND OF THE INVENTION

In the chronic disease diabetes mellitus (diabetes), the body loses the ability to properly produce or respond to the hormone insulin so that cells of the peripheral tissues fail to actively take up glucose from the blood for use or storage. In the diabetic individual, the level of glucose in the peripheral blood can become elevated (hyperglycaemia) and typically remains so unless some form of intervention is employed (e.g., administration of exogenous insulin) to return glucose in the blood to normal levels. Left unchecked, the hyperglycaemia of diabetic individuals can result in shock, organ degeneration or failure (e.g., kidney failure, blindness, nerve disease, cardiovascular disease), tissue necrosis (e.g., requiring foot amputation), and even death.

Two major forms of diabetes are type 1 and type 2 diabetes. Type 1 diabetes, which was previously known as insulin-dependent diabetes mellitus (IDDM) or juvenile onset diabetes, is an autoimmune disease in which the body destroys the insulin-producing β cells (islet cells) of the pancreas resulting in an absolute requirement for daily administration of exogenous insulin to maintain normal blood glucose levels. Type 1 diabetes usually is diagnosed in children and young adults, but can occur at any age. Type 1 diabetes accounts for 5-10% of diagnosed cases of diabetes.

By far the more prevalent form of diabetes is type 2 diabetes, which was previously known as non-insulin-dependent diabetes mellitus (NIDDM). Type 2 diabetes was also previously known as adult-onset diabetes, however, this form of diabetes is becoming increasingly prevalent in the growing population of overweight and clinically obese children and young adults. Type 2 diabetes accounts for approximately 90-95% of all diagnosed cases of diabetes. Type 2 diabetes typically begins with insulin resistance, a disorder in which the body's cells do not respond to insulin properly, followed by a gradual loss on part of the pancreas to produce and secrete insulin. Type 2 diabetes is associated with a variety of factors including older age, obesity, family history of diabetes, history of gestational diabetes, impaired glucose metabolism, physical inactivity, and various races or ethnicities. Individuals with type 2 diabetes must attempt to control their blood glucose level with careful diet, exercise and weight reduction, and additional medications.

Major factors contributing to the pro-atherogenic state in diabetes, particularly type 2 diabetes mellitus (DM2), include dyslipidemia, hyperglycemia, hypertension, visceral obesity and insulin resistance (1,2). Observational studies have clearly demonstrated the importance of diabetic dyslipidemia in contributing to atherogenesis in diabetes, illustrated by the fact that the correlation between low density lipoproteins (LDL) as well as high density lipoproteins (HDL) versus cardiovascular events outweighs that of fasting plasma glucose (3). Statin intervention studies have revealed a clear benefit of statin treatment on reduction of cardiovascular events in DM2 (4, 5); however, in spite of this impressive achievement, the majority of DM2 patients will still suffer from cardiovascular events even when using statins (6).

During the last two decades, endothelial dysfunction has emerged as one of the earliest stages of atherogenesis. Endothelial dysfunction, which is a hallmark in all diabetic patients (ie both type 1 and 2) has been shown to have predictive value for future cardiovascular events (7-9). In line with the multi-factorial pathogenesis of diabetes-induced vascular disease (10, 11), numerous therapeutic interventions have been evaluated for their potential to improve endothelial function in DM2 patients (9, 12). Surprisingly, whereas endothelial function could be fully restored by statin therapy in dyslipidemic patients (13), several studies have demonstrated that even intensive statin treatment cannot normalize vascular dysfunction in DM2 (14, 15). The latter emphasizes possibilities for additional therapeutic modalities in this high risk group.

High-density lipoproteins (HDLs) represent a broad group of mostly spheroidal plasma lipoproteins, which exhibit considerable diversity in their size, apolipoprotein (apo) and lipid composition. HDL particles fall into the density range of 1.063-1.21 g/ml (16) and as they are smaller than other lipoproteins, HDLs can penetrate between endothelial cells more readily allowing relatively high concentrations to accumulate in tissue fluids (17). The major apolipoprotein of almost all plasma HDLs is apo A-I, which in association with phospholipids and cholesterol, encloses a core of cholesteryl esters (16). Nascent (i.e. newly synthesised) HDLs secreted by the liver and intestine contain no cholesteryl esters and are discoidal in shape (16). The negative association of plasma HDL concentration with coronary artery disease has been well documented in epidemiological studies (18). Although experiments in animals have demonstrated an anti-atherogenic activity of HDLs (19), it is not yet known whether this protective effect is related to the role of the lipoprotein in reverse cholesterol transport or to a different mechanism. The mechanism/mechanisms via which HDLs provide these cardioprotective actions are not clearly understood, but may include a role for HDLs in reverse transport of cholesterol from peripheral tissues to the liver, inhibition of the oxidation of low-density lipoproteins, or modulation of vasodilatation and platelet activation mediated by changes in the production of prostacyclin (20). HDLs can also activate endothelial nitric oxide (NO) synthase subsequent to its interaction with scavenger receptor-B 1 (SR-B1).

In view of the emerging data on the NO promoting effects of HDL, compounds with HDL-increasing capacity are of particular interest (21-24). Indeed, in DM2 patients HDL is positively associated with endothelium-dependent vasomotor responses (8). In work leading to the present invention, the inventors have evaluated whether and to what extent HDL increase upon infusion of exogenous reconstituted HDL (rHDL) would translate into an improvement of vascular function. ApoA-I levels and endothelial function were assessed both acutely (4 hours after infusion) as well as 7 days after infusion of rHDL in DM2 and matched controls.

Bibliographic details of the publications referred to in this specification are referenced at the end of the description. The reference to any prior art document in the specification is not, and should not be taken as, an acknowledgment or any form of suggestion that the document forms part of the common general knowledge.

SUMMARY OF THE INVENTION

Throughout this specification and the claims which follow, unless the context requires otherwise, the word "comprise", and or variations such as "comprises" or "comprising", will be understood to imply the inclusion of a stated integer or step or group of integers or steps but not the exclusion of any other integer or step or group of integers or steps.

In one aspect, the present invention provides a method for the treatment of endothelial dysfunction in a diabetic patient, which comprises administration (preferably parenteral administration) to the patient of an effective amount of high density lipoprotein (HDL).

In another aspect, the present invention provides the use of high density lipoprotein (HDL) in the manufacture of a medicament for administration (preferably parenteral administration) to a diabetic patient for the treatment of endothelial dysfunction in the patient.

In yet another aspect, the present invention provides an agent for administration (preferably parenteral administration) in the treatment of endothelial dysfunction in a diabetic patient, which comprises high density lipoprotein (HDL).

DETAILED DESCRIPTION OF THE INVENTION

Patients with diabetes, particularly type 2 diabetes mellitus (DM2), are characterized by a marked increase in cardiovascular risk. Systemic endothelial dysfunction, a hallmark in DM2, predicts future risk for cardiovascular events. In view of the relation between HDL and the NO pathway, the present inventors have evaluated the effect of rHDL infusion on endothelial function in DM2. Specifically, in 7 DM2 patients and 7 normolipidemic controls, endothelial function was assessed using venous occlusion plethysmography. Forearm blood flow (FBF) responses to intra-arterial infusion of the endothelium-dependent and independent vasodilators serotonin (5HT) and sodium nitroprusside, respectively, and the inhibitor of nitric oxide synthase NG-monomethyl-1-arginine (L-NMMA) were measured, both before, 4 hours after and 1 week after infusion of rHDL (80 mg/kg based on protein).

At baseline HDL was similar in DM2 versus controls ($1.1\pm0.2$ vs. $1.2\pm0.3$ mmol/L, ns). 5HT-induced vasodilation (max $17\pm10\%$) and L-NMMA induced vasoconstriction (max$-17\pm15\%$) were reduced in DM2 versus controls (5-HT $114\pm22$ and L-NMMA $-48\pm5\%$, both $p<0.05$). rHDL infusion raised apoA-I levels ($1.2\pm0.2$ to $2.8\pm0.4$ vs. $1.2\pm0.2$ to $2.7\pm0.4$ g/L, $p<0.01$) in DM2 and controls, respectively and restored FBF responses to 5HT ($86\pm22\%$, $p<0.05$) and L-NMMA ($-45\pm9\%$, $p<0.01$) in DM2. This effect persisted 7 days after infusion (5HT; $80\pm25\%$, $p<0.05$ and L-NMMA $-37\pm7\%$, $p<0.01$ compared to baseline). rHDL infusion had no effect in controls. Accordingly, this work demonstrates that acute HDL increase improves endothelial function in DM2 and that the improvement persists for at least 7 days in spite of return-to-baseline of HDL concentration.

In one aspect, the present invention provides a method for the treatment of endothelial dysfunction in a diabetic patient, which comprises administration to the patient of an effective amount of high density lipoprotein (HDL).

Preferably, the administration is parenteral administration.

Reference herein to "treatment" is to be considered in its broadest context. The term "treatment" does not necessarily imply that a subject is treated until total recovery. Accordingly, treatment includes amelioration of the symptoms of a particular condition or disorder as well as reducing the severity of, or eliminating a particular condition or disorder.

As used herein, references to "treatment of endothelial dysfunction" are to be considered as references to improvement of endothelial function in treatment of disorders which are related to endothelial dysfunction. Such disorders include both macrovascular disorders (relating to the large blood vessels) such as transient ischaemic attack, stroke, angina, myocardial infarction, cardiac failure, and peripheral vascular disease, as well as microvascular disorders (relating to the small blood vessels) such as diabetic retinopathy (non-proliferative, proliferative, macular oedema), microalbuminuria, macroalbuminuria, end stage renal disease, erectile dysfunction, autonomic neuropathy, peripheral neuropathy, osteomyelitis and lower limb ischaemia.

References herein to a "diabetic" patient are to be understood as a reference to a patient suffering from either type 1 diabetes (DM1) or type 2 diabetes (DM2).

In accordance with the present invention, HDL is administered to a diabetic patient. The term "HDL" as used herein relates to all forms of high density lipoproteins and includes mature HDL, nascent HDL or reconstituted HDL (rHDL) or any mixture thereof, as well as rHDL produced from recombinant apolipoprotein or an analogue thereof with functional relationship to nascent or reconstituted HDL. Such analogues include functional peptides derived from the apolipoprotein (Apo) structure such as those described in International Patent Publications Nos. WO 99/16459 and WO 99/16408, the contents of which are incorporated herein by reference.

The high density lipoproteins comprise a protein component, and lipid. The proteins are preferably apolipoproteins, e.g. human apolipoproteins such as apolipoprotein apolipoprotein A-II (apoA-II) or apolipoprotein A-IV (apoA-IV) or recombinant apolipoproteins, or functionally homologous peptides with similar properties. Suitable lipids are phospholipids, preferably phosphatidyl choline, optionally mixed with other lipids (cholesterol, cholesterol esters, triglycerides, sphingolipids, or other lipids). The lipids may be synthetic lipids, naturally occurring lipids or combinations thereof.

Preferably, the HDL is reconstituted HDL.

Production of reconstituted HDL is described, by way of example, in U.S. Pat. No. 5,652,339 and by Matz and Jonas (25) and Lerch et al. (26). Production of rHDL with recombinant apolipoproteins is described, by way of example, in European Patent No. EP 469017 (in yeast), U.S. Pat. No. 6,559,284 (in *E. coli*), and International Patent Publications Nos. WO 87/02062 (in *E. coli*, yeast and Cho cells) and WO 88/03166 (in *E. coli*). The contents of each of these documents are incorporated herein by reference.

The HDL is administered in an effective amount. An "effective amount" means an amount necessary at least partly to attain the desired response, or to delay the onset or inhibit progression or halt altogether, the onset or progression of the particular condition or disorder being treated. The amount varies depending upon the health and physical condition of the individual to be treated, the racial background of the individual to be treated, the degree of protection desired, the formulation of the composition, the assessment of the medical situation, and other relevant factors. It is expected that the amount will fall in a relatively broad range that can be determined through routine trials.

Preferred HDL dosage ranges are from 0.1-200 mg, more preferably 10-80 mg, HDL (weight based on apolipoprotein) per kg body weight per treatment. For example, the dosage of HDL which is administered may be about 0.2-100 mg HDL per kg body weight (weight based on apolipoprotein) given as an intravenous injection and/or as an infusion for a clinically necessary period of time, e.g. for a period ranging from a few minutes to several hours, e.g. up to 24 hours. If necessary, the HDL administration may be repeated one or several times. The actual amount administered will be determined both by the nature of the condition or disorder which is being treated and by the rate at which the HDL is being administered.

Preferably, the patient is a human, however the present invention extends to treatment and/or prophylaxis of other mammalian patients including primates, livestock animals (e.g. sheep, pigs, cattle, horses, donkeys), laboratory test animals (e.g. mice, rabbits, rats, guinea pigs), companion animals (e.g. dogs, cats) and captive wild animals.

In accordance with the present invention, the HDL is preferably administered to a patient by a parenteral route of administration. Parenteral administration includes any route of administration that is not through the alimentary canal (that is, not enteral), including administration by injection, infusion and the like. Administration by injection includes, by way of example, into a vein (intravenous), an artery (intraarterial), a muscle (intramuscular) and under the skin (subcutaneous). The HDL may also be administered in a depot or slow release formulation, for example, subcutaneously, intradermally or intramuscularly, in a dosage which is sufficient to obtain the desired pharmacological effect.

Compositions suitable for parenteral administration conveniently comprise a sterile aqueous preparation of the active component which is preferably isotonic with the blood of the recipient. This aqueous preparation may be formulated according to known methods using suitable dispersing or wetting agents and suspending agents. The sterile injectable preparation may also be a sterile injectable solution or suspension in a non-toxic parenterally-acceptable diluent or solvent, for example as a solution in a polyethylene glycol and lactic acid. Among the acceptable vehicles and solvents that may be employed are water, Ringer's solution, suitable carbohydrates (e.g. sucrose, maltose, trehalose, glucose) and isotonic sodium chloride solution. In addition, sterile, fixed oils are conveniently employed as a solvent or suspending medium. For this purpose, any bland fixed oil may be employed including synthetic mono- or di-glycerides. In addition, fatty acids such as oleic acid find use in the preparation of injectables.

The formulation of such therapeutic compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in Remington's Pharmaceutical Sciences, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer.

The present invention also provides the use of high density lipoprotein (HDL) in the manufacture of a medicament for administration, preferably parenteral administration, to a diabetic patient for the treatment of endothelial dysfunction in the patient.

In yet another aspect, the invention provides an agent for administration, preferably parenteral administration, in the treatment of endothelial dysfunction in a diabetic patient, which comprises high density lipoprotein (HDL).

The present invention is further illustrated by the following non-limiting Example.

Example

I. Methods

Seven non smoking patients with uncomplicated DM2 (4 men and 3 women) and 7 non smoking age- and sex matched normolipidemic control subjects (4 men and 3 women) were enrolled. Inclusion criteria for patients with DM2 were as follows: (1) fasting plasma glucose>7.0 mmol/L, (2) under treatment with diet and metformine; (3) not using exogenous insulin; (4) mild dyslipidemia with plasma triglycerides and LDL cholesterol levels of less than 2.0 and 15 mmol/l, respectively. The presence of macrovascular disease, defined as ECG abnormalities, abnormal ankle-brachial index or a history of cardiac, cerebral of peripheral vascular events and autonomic neuropathy were exclusion criteria for either patients or control subjects. All female patients were postmenopausal and were not on hormone replacement therapy. The median duration of diabetes was $5.2 \pm 1.2$ [mean$\pm$SD] years. Assessments were performed at least 4 weeks after the cessation of vasoactive medication, such as ACE inhibitors, angiotensin receptor blockers, calcium channel blockers, aspirin, NSAIDs, and vitamin supplementation. None of the patients used statin therapy. Alcohol, caffeine and metformin were withheld within 12 hours before the study. All subjects gave written informed consent and approval was obtained from the internal review board of the Academic Medical Center (AMC), University of Amsterdam, Amsterdam, The Netherlands. The study was carried out in accordance with the principles of the declaration of Helsinki.

Study Protocol

Vascular function was assessed at baseline and after rHDL infusion using venous occlusion strain-gauge plethysmography as previously published (EC-4; Hokanson Inc, Bellevue, USA) (27). Measurements were performed in a quiet room with a constant temperature (22° C. to 24° C.) and started at 08:00 a.m. Subjects remained in supine position throughout the study. The brachial artery of the nondominant arm was cannulated with a 20-gauge, flexible, polyurethane catheter (Arrow Inc, Reading, USA). Insertion was followed by a 30 minute interval of saline infusion to allow for re-establishing baseline conditions. Thereafter, forearm blood flow (FBF), expressed as milliliters per minutes per 100 mL of forearm tissue volume (FAV), and was measured simultaneously in both arms. A microcomputer-based R-wave-triggered system for online monitoring was used. During each measurement, blood pressure cuffs around both upper arms were inflated (40 mm Hg) by use of a rapid cuff inflator. Simultaneously, bilateral wrists cuffs were inflated to above-systolic blood pressure to exclude hand circulation (200 mmHg). Intra-arterial blood pressure and heart rate were monitored continuously. Next, FBF response to cumulative doses of the endothelium-dependent vasodilator serotonin (5HT, Sigma; 0.6, 1.8, and 6 ng·100 mL $FAV^{-1} \cdot min^{-1}$), the endothelium-independent vasodilator sodium nitroprusside (SNP, Spruyt Hillen; 6, 60, 180, and 600 ng·100 mL $FAV^{-1} \cdot min^{-1}$), and the competitive inhibitor of endothelial NO synthase (eNOS) $N^G$-monomethyl-L-arginine (L-NMMA, Kordia; 50, 100, 200, and 400 µg·100 mL $FAV^{-1} \cdot min^{-1}$) was measured. Infusion blocks of serotonin and sodium nitroprusside were administered in randomized order, followed by L-NMMA infusion. All infusates were prepared in the pharmacy of the AMC in accordance with good manufacturing practice (GMP) guidelines. Agents were administered intra-arterially for 6, 4, and 8 minutes at each dose, respectively, with a constant-rate infusion pump. Six measurements during the last 2 minutes of each infusion block were averaged to determine mean FBF. The 3 different infusion blocks proceeded after a 15-minute rest period or until FBF had returned to baseline. Subsequently, a venous catheter was inserted in the contralateral arm for administration of rHDL at a dose of 80 mg/kg body weight over a period of 4 hours (CSL Behring, Bern, Switzerland) (26, 27). Thereafter, the infusion blocks were repeated. Patients were then asked not restart their medication (besides metformin) and had to return 7 days after rHDL infusion to repeat endothelial function measurements.

Laboratory Assessments

Blood samples were drawn from the subjects after a 12-hour overnight fast, immediately, 4 hours and 7 days after rHDL infusion. After centrifugation within 1 hour after collection, aliquots were snap-frozen in liquid nitrogen and stored at −80° C. until the assays were performed. All measurements were performed at the Vascular and Clinical laboratory of the Academic Medical Center, University Hospital of Amsterdam. ALAT and ASAT were measured by pyridoxalphosphate activation assay (Roche Diagnostics, Basel, Switzerland). HbA1c was measured by HPLC (Reagens Bio-Rad Laboratories B.V., the Netherlands) on a Variant II (Bio-Rad Laboratories). Plasma glucose was assessed in duplicate using the hexokinase method (Gluco-quant on Hitachi 917; Hitachi). Plasma triglycerides, total cholesterol, LDL and HDL levels were determined by standard enzymatic methods (Roche Diagnostics, Basel, Switzerland). Plasma levels of apoA-I and apoB were assessed on stored plasma by rate nephelometry.

Statistical Analysis

All results of clinical parameters, including plethysmographic data, are expressed as mean±SD. Descriptive statistics between the 2 groups were compared by means of 2-tailed independent Student's t test. FBF was averaged over 6 consecutive recordings during the last 2 minutes of each infusion step. FBF recordings made in the first 30 seconds after wrist-cuff inflation were not used for analysis. Statistical analysis of FBF measurements, HDL quality and inflammatory markers for individual subjects between the 2 groups was performed by 2-way ANOVA for repeated measures. A probability value of $P<0.05$ was considered significant and a value of $P<0.01$ as highly significant.

II Results

Subject characteristics are listed in Table 1. Baseline FBFs were not significantly different between patients and control subjects (Table 1). As expected, plasma levels of fasting plasma glucose ($P<0.01$), hemoglobin $A_{1c}$ ($P<0.01$), triglycerides ($P<0.01$) and apoB ($P<0.05$) were higher in DM2 patients. HDL-C and apoA-I levels were comparable between DM2 patients and controls. After rHDL infusion, plasma apoA-I increased in DM2 and control after 4 hours (1.2±0.2 to 2.8±0.4 versus 1.2±0.2 to 2.7±0.4 g/L, $p<0.01$ respectively), whereas a slight increase remained in DM2 patients 7 days after infusion (1.5±0.3 g/L, $p<0.05$ compared to baseline). Plasma apoB levels were higher in DM2 compared to controls and were not affected by rHDL infusion (1.0±0.3 to 0.9±0.3 versus 0.7±0.2 to 0.7±0.2 g/L, ns, respectively).

Acute and Long Term Effects of rHDL Infusion on NO Bio-Availability

Figure 1:
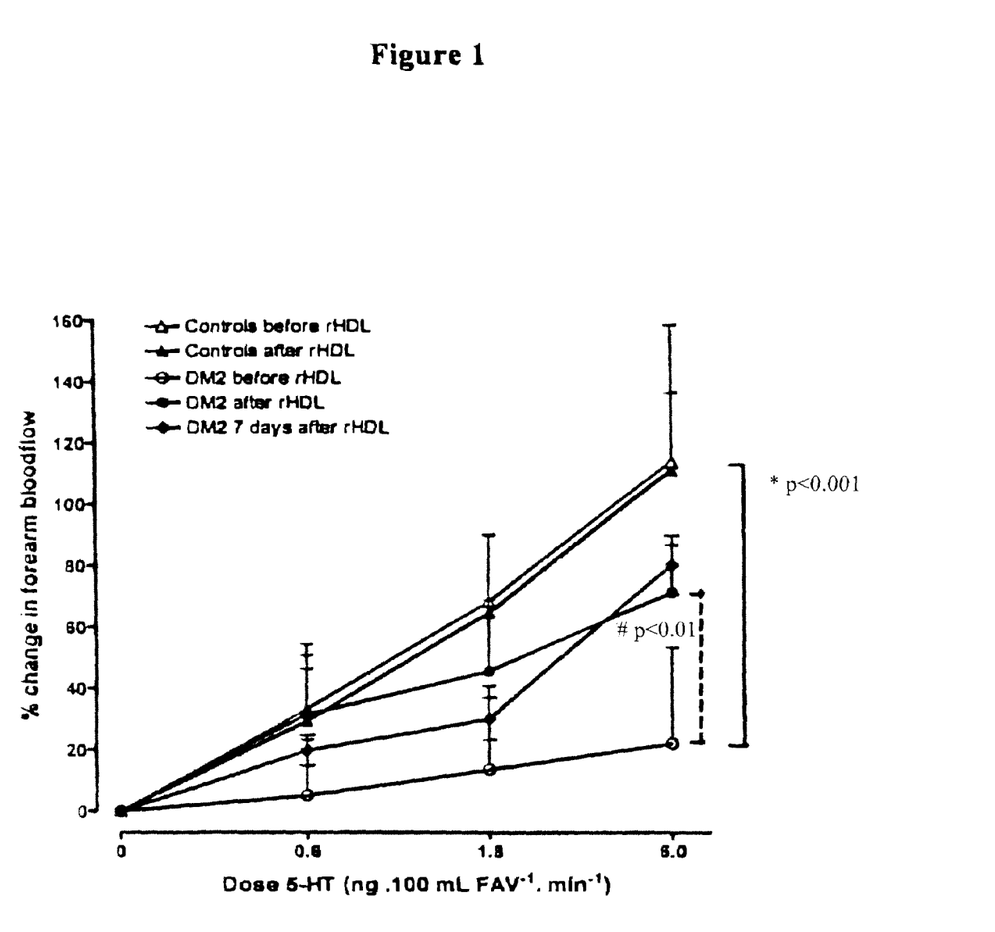
FIG. 1 is a diagram which shows that intra-arterial infusion of the endothelium-dependent vasodilator serotonin increased forearm blood flow (FBF) in a dose-dependent manner in healthy volunteers and patients with DM2. At baseline, the FBF response to serotonin was attenuated in DM2 compared to controls ($p<0.001$). After rHDL infusion, FBF response to serotonin increased significantly, but did not reach levels comparable to controls ($p<0.01$). Improvement in endothelium-dependent vasodilation persisted 7 days after rHDL infusion ($p<0.01$). rHDL infusion did not affect serotonin response in controls.

Intra-arterial infusion of the endothelium-dependent vasodilator serotonin increased FBF in a dose-dependent manner in both groups. At baseline, the FBF response to serotonin was attenuated in DM2 compared to controls ($p<0.001$, FIG. 1). After rHDL infusion, FBF response to serotonin increased significantly, but did not reach levels comparable to controls ($p<0.01$, FIG. 1). Interestingly, improvement in endothelium-dependent vasodilation persisted 7 days after rHDL infusion ($p<0.01$, FIG. 1). rHDL infusion did not affect serotonin response in controls (FIG. 1).

Figure 2:
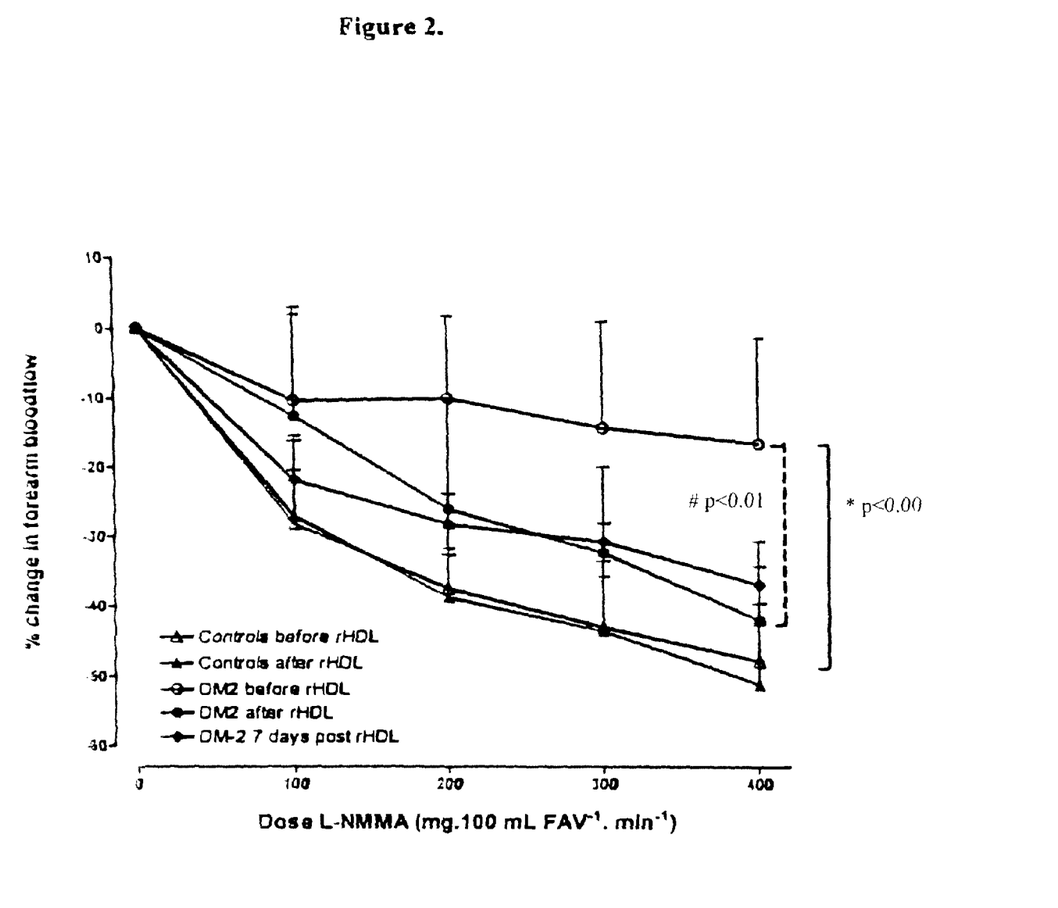
FIG. 2 is a diagram which shows that at baseline the vasoconstrictor response to L-NMMA, reflecting basal nitric oxide (NO) activity, was blunted in DM2 patients compared to controls ($p<0.001$). After rHDL infusion, the L-NMMA constrictor response was improved, again still present 7 days after infusion ($p<0.01$). In line with the serotonin data, rHDL infusion had no effect on L-NMMA response in control subjects.

At baseline the vasoconstrictor response to L-NMMA, reflecting basal NO activity, was blunted in DM2 patients compared to controls ($p<0.001$, FIG. 2). After rHDL infusion, the L-NMMA constrictor response was improved, again still present 7 days after infusion ($p<0.01$, FIG. 2). In line with the serotonin data, rHDL infusion had no effect on L-NMMA response in control subjects (FIG. 2).

Figure 3:
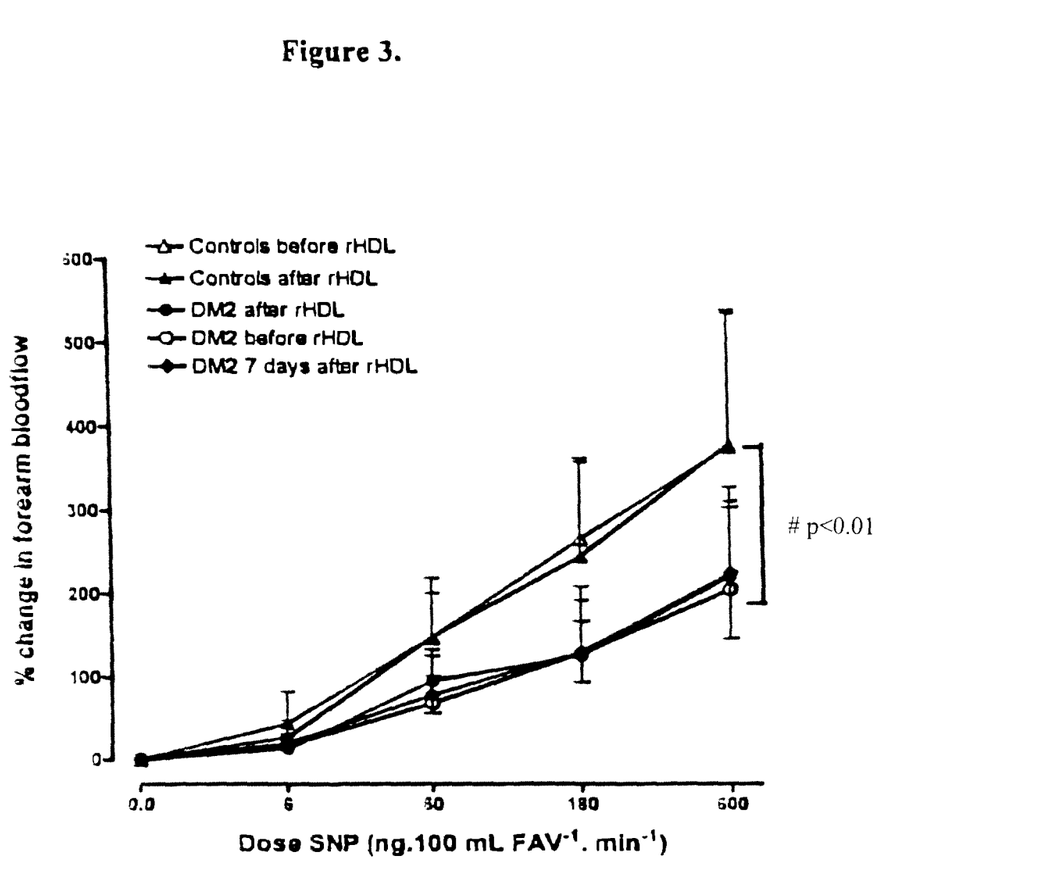
FIG. 3 is a diagram which shows that endothelium-independent vasodilation in response to sodium nitroprusside was lower in DM2 versus controls ($p<0.01$) and rHDL infusion did not show effect on SNP vasodilator response both in patients and controls

Finally, endothelium-independent vasodilation in response to SNP was lower in DM2 versus controls ($p<0.01$, FIG. 3) and rHDL infusion did not show effect on SNP vasodilator response both in patients and controls.

III Discussion

The present study shows that both basal and stimulated NO activity are severely compromised in DM2 patients compared to age and sex-matched controls. Interestingly, despite near normal HDL levels in DM2 patients, infusion of rHDL significantly improved endothelial function. This improvement persisted up to 7 days after rHDL infusion, at which time HDL levels had already returned towards baseline values. These data imply that HDL increasing strategies may offer therapeutic benefit in DM2, even if HDL-C levels are not clearly decreased in these patients.

Vascular Function at Baseline

In line with previous studies (8, 9, 12), the presence of both impaired basal NO-activity as well as attenuated NO-release in DM2 upon receptor-mediated stimulation is confirmed. Several mechanisms have been shown to contribute to endothelial dysfunction in diabetes. Decreased bio-availability of the essential cofactor tetrahydrobiopterin (BH4) is associated with uncoupling of endothelial NO-synthase leading to direct production of oxygen radicals instead of NO by eNOS (28-30). Other sources may also contribute to increased radical production, including NADPH-oxidase as well as mitochondrial uncoupling (10). The pivotal role of ROS in diabetic vascular dysfunction has been underscored by interventions studies, reporting full restoration of endothelial function upon intra-arterial infusion of high concentration of antioxidants (9, 12).

Effect of rHDL Infusion on Vascular Function

Infusion of rHDL was associated with a rapid improvement of both basal NO activity as well as receptor-stimulated NO-activity, within a few hours after infusion. A first explanation would be that rHDL increases NO production. Nitric oxide (NO) is synthesized by eNOS through the conversion of L-arginine to L-citrulline. Its activity is regulated by complex signalling transduction pathways including activation of the kinases that alter the phosphorylation of eNOS, i.e. MAP kinase and akt-kinase signalling, or increasing intracellular $Ca^{2+}$ content followed by calcium-calmodulin dependent activation of eNOS (33). Yuhanna showed that binding of apoA-I to the endothelial scavenger receptor B-1 was accompanied by enhanced endothelium-dependent relaxation responses in aortas (24), largely due to akt and MAP-kinase activation (32). In addition, HDL also has the capacity to upregulate membrane content of eNOS within endothelial cells by preserving eNOS protein stability as well as by preventing eNOS translocation from the cell membrane to intracellular organelles (23). All these effects may have contributed to the increase in basal NO-availability, assessed as increased vasoconstrictor responses to the competitive NO-inhibitor L-NMMA, after rHDL infusion. In contrast, the aforementioned mechanisms cannot fully explain the increase in serotonin-dependent, receptor-stimulated NO availability, which is dependent upon calcium-calmodulin activation of eNOS (31). Since serotonin binding to the endothelial $5HT_{2A}$ receptor (33) is unlikely to change upon rHDL infusion, decreased degradation of NO by oxygen radicals provides a second major pathway which can contribute to increased NO-bioavailability. Indeed, HDL has potent antioxidative properties, not in the least due to the presence of enzymes such as paraoxonase and platelet-activating factor hydrolase on the HDL particle (23).

Long-Term Effects of rHDL on Vascular Function

Strikingly, endothelium dependent vasodilation was still significantly improved 1 week after rHDL infusion. In contrast, both apoAI as well as HDL levels had almost returned towards pre-infusion levels. Noticeably, at baseline HDL levels in DM2 were also not significantly different from those in control subjects. In contrast, rHDL infusion had no effect whatsoever on vascular function in controls. These data imply that, in spite of normal HDL concentration, HDL quality may be impaired in DM2. In fact, loss of HDL protective effects in DM2 has been partly attributed to non-enzymatic glycation of predominantly leucine chains in HDL. Glycation of apoAI-HDL compromises the ability of HDL to protect LDL from oxidative damage, amongst other by loss of PON-1 activity (34). In addition, glycated HDL reduces eNOS expression within the endothelium, leading to impaired NO-producing capacity (35). Indeed, antioxidative activity level of HDL in DM2 patients are intimately linked to oxidative stress levels and glycemic control (36).

Study Limitations

Since an effect of rHDL was not seen 4 hours after infusion in the control group, the vascular function studies were not repeated after 7 days in the control group. Consequently, the vascular function data on day 7 in DM2 patients were compared to baseline and day 1 observations in controls. However, since the major conclusion on vascular function relates to the persistent improvement compared to DM2 patients at baseline, lack of day 7 study in controls has no impact on the conclusions drawn in the present study. Second, although only a relatively small group of DM2 patients was studied, the fact that a significant improvement was found already in a limited group of patients and reproducibly after 4 hours and 1 week, is supportive of a clear conclusion on the effect of HDL on vascular function in DM2 patients, in spite of the small sample size.

Clinical Implications for DM2 Patients

Statins are the central paradigm for cardiovascular preventive strategies. However, in view of the large number of events not prevented during statin therapy, the search for optimal combination therapies is in full progress. The promise of HDL increasing strategies is expanding rapidly. The strong inverse relationship between HDL-C and cardiovascular events is a consistent finding in both non-diabetic as well as diabetic patients. Unfortunately, solid data providing evidence for reduction of cardiovascular risk following HDL-increasing interventions are scarce, predominantly due to lack of selective and potent HDL increasing compounds (37).

Recent data have shown that 5 weekly infusions of rHDL produced with a variant apolipoprotein (apoA-I Milano) were able to slow progression or even induce regression of coronary atheroma volume in patient with recent myocardial infarction (38). In line with such a rapid effect, both experimental as well as in vivo studies have shown that the anti-atherogenic capacity of HDL is not merely restricted to its role in reverse cholesterol transport. The present observation of acute and persistent restoration of endothelial dysfunction in DM2 lends further support to effects of HDL beyond its role in reverse cholesterol transport. This supports a role for HDL increase in DM2 even if HDL levels are not clearly decreased.

TABLE 1

| | DM2 (n = 7) | CON (n = 7) |
|---|---|---|
| Age, years | 53.6 ± 3.0 | 48.6 ± 15.1 |
| Sex (female/male) | 3/4 | 3/4 |
| BMI, kg/m² | 28.9 ± 2.4 | 25.6 ± 3.6 |
| Smoking (y/n) | 0/7 | 0/7 |
| Systolic blood pressure, mmHg | 148 ± 12 | 135 ± 16 |
| Diastolic blood pressure, mmHg | 78 ± 13 | 83 ± 9 |
| Heart Rate, bpm | 65 ± 5 | 61 ± 4 |
| Fasting plasma glucose, (mmol/L) | 8.3 ± 1.2 | 5.2 ± 0.4# |
| HbA1c, % | 7.1 ± 0.3 | 5.4 ± 0.3# |
| Total Cholesterol, mmol/L | 5.6 ± 0.4 | 5.3 ± 0.4 |
| LDL-C, mmol/L | 2.9 ± 0.6 | 3.0 ± 0.7 |
| HDL-C, mmol/L | 1.1 ± 0.2 | 1.2 ± 0.3 |
| ApoA-I, g/L | 1.2 ± 0.1 | 1.2 ± 0.2 |
| ApoB, g/L | 1.1 ± 0.3 | 0.8 ± 0.2* |
| Triglycerides, mmol/L | 1.5 ± 0.4 | 0.8 ± 0.3# |
| Basal FBF, ml · 100 mL $FAV^{-1}$ · min | 4.1 ± 2.0 | 2.6 ± 0.9 |

*p < 0.05,
p < 0.01

REFERENCES

1. Haffner S M. "Coronary heart disease in patients with diabetes". N Engl J Med (2000); 342 (14):1040-2.
2. Rohrer L, Hersberger M, von Eckardstein A. "High density lipoproteins in the intersection of diabetes mellitus, inflammation and cardiovascular disease." Curr Opin Lipidol. (2004); 15 (3):269-78.
3. Turner R C, Millns H, Neil H A et al. "Riskfactors for coronary artery disease in non-insulin dependent diabetes mellitus: United Kingdom Prospective Diabetes Study (UKPDS:23)". BMJ (1998); 316:823-828.
4. Pyorala K, Pedersen T R, Kjekshus J, Faergeman O, Olsson A G, Thorgeirsson G. "Cholesterol lowering with simvastatin improves prognosis of diabetic patients with coronary heart disease. A subgroup analysis of the Scandinavian Simvastatin Survival Study (4S)". *Diabetes Care* (1997); 20 (4):614-20.
5. Colhoun H M, Betteridge D J, Durrington P N, Hitman G A, Neil H A, Livingstone S J, Thomason M J, Mackness M I, Charlton-Menys V, Fuller J H; CARDS investigators. Primary prevention of cardiovascular disease with atorvastatin in type 2 diabetes n the Collaborative Atorvastatin Diabetes Study (CARDS): multicentre randomised placebo-controlled trial. *Lancet* (2004); 364 (9435):685-96.
6. Cheung B M, Lauder I J, Lau C P, Kumana C R. "Meta-analysis of large randomized controlled trials to evaluate the impact of statins on cardiovascular outcomes." *Br J Clin Pharmacol*. (2004); 57 (5):640-51.
7. Schachinger V, Britten M B, Zeiher A M. "Prognostic impact of coronary vasodilator dysfunction on adverse long-term outcome of coronary heart disease." *Circulation* (2000); 101:1899-1906.
8. Woodman R J, Playford D A, Watts G F. "Basal production of nitric oxide (NO) and non-NO vasodilators in the forearm microcirculation in Type 2 diabetes: associations with blood pressure and HDL cholesterol." *Diabetes Res Clin Pract*. (2006); 71 (1):59-67.
9. van Etten R W, de Koning E J, Verhaar M C, Gaillard C A, Rabelink T J. "Impaired NO-dependent vasodilation in patients with Type II (non-insulin-dependent) diabetes mellitus is restored by acute administration of folate." *Diabetologia* (2002); 45 (7):1004-10.
10. Brownlee M. "Biochemistry and molecular cell biology of diabetic complications." *Nature* (2001); 414 (6865): 813-20.
11. Du X, Edelstein D, Obici S, Higham N, Zou M H, Brownlee M. "Insulin resistance reduces arterial prostacyclin synthase and eNOS activities by increasing endothelial fatty acid oxidation." *J Clin Invest*. (2006); 116 (4):1071-80.
12. Ting H H, Timimi F K, Boles K S, Creager S J, Ganz P, Creager M A. "Vitamin C improves endothelium-dependent vasodilation in patients with non-insulin-dependent diabetes mellitus." *J Clin Invest*. (1996); 97 (1):22-8.
13. Stroes E S, Koomans H A, de Bruin T W, Rabelink T J. "Vascular function in the forearm of hypercholesterolaemic patients off and on lipid-lowering medication." *Lancet* (1995); 346 (8973):467-71.
14. van Etten R W, de Koning E J, Honing M L, Stroes E S, Gaillard C A, Rabelink T J. "Intensive lipid lowering by statin therapy does not improve vasoreactivity in patients with type 2 diabetes." *Arterioscler Thromb Vasc Biol*. (2002); 22 (5):799-804.
15. Balletshofer B M, Goebbel S, Rittig K, Enderle M, Schmolzer I, Wascher T C et al. "Intense cholesterol lowering therapy with a HMG-CoA reductase inhibitor does not improve nitric oxide dependent endothelial function in type-2-diabetes—a multicenter, randomised, double-blind, three-arm placebo-controlled clinical trial." *Exp Clin Endocrinol Diabetes* (2005); 113 (6):324-30.
16. Cockerill G W, Reed S: High-density lipoprotein: Multipotent effects on cells of the vasculature. *Int. Rev. Cytol.* (1999); 188: 257-297.
17. Nanjee M N, Doran J E, Lerch P G, Miller N E: Acute effects of intravenous infusion of apolipoprotein A-I/phosphatidylcholine discs on plasma lipoproteins in human. *Arterioscler. Thromb. Vasc. Biol*. (1999); 19: 979-989.
18. Gordon D J, Probsfield J L, Garrison R J: High-density lipoprotein cholesterol and cardiovascular disease: four prospective American studies. *Circulation* (1989); 79:8-15.
19. Paszty C, Maeda N, Verstuyft J: Apolipoprotein AI transgene corrects apolipoprotein E-deficiency-induced atherosclerosis in mice. *J. Clin. Invest*. (1998); 94: 899-903.
20. Tangirala R K, Tsukamoto K, Chun S H, Usher D, Pure E, Rader D J: Regression of atherosclerosis induced by liver-directed gene transfer of apolipoprotein A-1 in mice. *Circulation* (1999); 100: 1816-1822.
21. Bisoendial R J, Hovingh G K, El Harchaoui K, Levels J H, Tsimikas S, Pu K, Zwinderman A E, Kuivenhoven J A, Kastelein J J, Stroes E S. "Consequences of cholesteryl ester transfer protein inhibition in patients with familial hypoalphalipoproteinemia." *Aterioscler Thromb Vasc Biol*. (2005); 25 (9); e133-34.
22. Brousseau M E, Schaefer E J, Wolfe M L, Bloedon L T, Digenio A G, Clark R W, Mancuso J P, Rader D J. "Effects of an inhibitor of cholesteryl ester transfer protein on HDL cholesterol." *N Engl J Med*. (2004); 350 (15):1505-1515.
23. Mineo C, Deguchi H, Griffin J H, Shaul P W. "Endothelial and antithrombotic actions of HDL." *Circ Res*. (2006); 98 (11):1352-64.
24. Yuhanna I S, Zhu Y, Cox B E, Hahner L D, Osborne-Lawrence S, Lu P, Marcel Y L, Anderson R G, Mendelsohn M E, Hobbs H H, Shaul P W. "High-density lipoprotein binding to scavenger receptor-B1 activates endothelial nitric oxide synthase." *Nat Med* (2001); 7 (7):853-7.
25. Matz C E, Jonas A. "Micellar complexes of human apolipoprotein A-1 with phosphatidylcholines and cholesterol prepared from cholate-lipid dispersion." *J. Biol. Chem*. (1982); 257:4535-4540.
26. Lerch P G, Fortsch V, Hodler G, Bolli R. "Production and characterization of a reconstituted high density lipoprotein for therapeutic applications." *Vox Sang*. (1996); 71 (3): 155-64.
27. Bisoendial R J, Hovingh G K, Levels J H, Lerch P G, Andresen I, Hayden M R, Kastelein J J, Stroes E S. "Restoration of endothelial function by increasing high-density lipoprotein in subjects with isolated low high-density lipoprotein." *Circulation* (2003); 107 (23):2944-8.
28. Stroes E, Kastelein J, Cosentino F, Erkelens W, Wever R, Koomans H, Luscher T, Rabelink T. "Tetrahydrobiopterin restores endothelial function in hypercholesterolemia." *J Clin Invest*. 1997; 99 (1):41-6.
29. Alp N J, Mussa S, Khoo J, Cai S, Guzik T, Jefferson A, Goh N, Rockett K A, Channon K M. "Tetrahydrobiopterin-dependent preservation of nitric oxide-mediated endothelial function in diabetes by targeted transgenic GTP-cyclohydrolase I overexpression." *J Clin Invest*. (2003); 112 (5):725-235.
30. Heitzer T, Krohn K, Alvers S, Meinertz T. "Tetrahydrobiopterin improves endothelium-dependent vasodilation by increasing nitric oxide activity in patients with type II diabetes mellitus." *Diabetologia* (2000); 43 (11):1435-8.
31. Govers R, Rabelink T J. "Cellular regulation of endothelial nitric oxide synthase." *Am J Physiol Renal Physiol*. (2001); 280 (2):F193-206.
32. Mineo C, Yuhanna I S, Quon M J, Shaul P W. "High density lipoprotein-induced endothelial nitric-oxide synthase activation is mediated by Akt and MAP kinases." *J Biol. Chem*. (2003); 278 (11):9142-9.
33. Takano S, Hoshino Y, Li L, Matsuoka I, Ono T, Kimura J. "Dual roles of 5-hydroxytryptamine in ischemia-reperfusion injury in isolated rat hearts." *J Cardiovasc Pharmacol Ther*. (2004); 9 (1):43-50.
34. Hedrick C C, Thorpe S R, Fu M X, Harper C M, Yoo J, Kim S M, Wong H, Peters A L. "Glycation impairs high-density lipoprotein function." *Diabetologia*. (2000); 43 (3):312-20.

35. Matsunaga T, Nakajima T, Miyazaki T, Koyama I, Hokari S, Inoue I, Kawai S, Shimomura H, Katayama S, Hara A, Komoda T. "Glycated high-density lipoprotein regulates reactive oxygen species and reactive nitrogen species in endothelial cells." *Metabolism* (2003); 52 (1):42-9.
36. Nobecourt E, Jacqueminet S, Hansel B, Chantepie S, Grimaldi A, Chapman M J, Kontush A. "Defective antioxidative activity of small dense HDL3 particles in type 2 diabetes: relationship to elevated oxidative stress and hyperglycaemia." *Diabetologia*. (2005); 48 (3):529-38.
37. Keech A, Simes R J, Barter P, Best J, Scott R, Taskinen M R et al; FIELD study investigators. "Effects of long-term fenofibrate therapy on cardiovascular events in 9795 people with type 2 diabetes mellitus (the FIELD study): randomised controlled trial." *Lancet* (2005); 366 (9500): 1849-61.
38. Nissen S E, Tsunoda T, Tuzcu E M, Schoenhagen P, Cooper C J, Yasin M, Eaton G M, Lauer M A, Sheldon W S, Grines C L, Halpern S, Crowe T, Blankenship J C, Kerensky R. "Effect of recombinant ApoA-I Milano on coronary atherosclerosis in patients with acute coronary syndromes: a randomized controlled trial." *JAMA* (2003); 290 (17):2292-300.

The invention claimed is:

1. A method for the treatment of endothelial dysfunction in a Type 2 diabetic patient, which comprises administering to a Type 2 diabetic patient suffering from endothelial dysfunction associated with a diabetes-induced macrovascular disorder, an amount of high density lipoprotein (HDL) effective to improve endothelial function, wherein said HDL is administered in a dosage range of from 0.2-100 mg per kg body weight of the patient per treatment, wherein each treatment is separated by at least 7 days.

2. The method of claim 1, wherein said diabetes induced macrovascular disorder is selected from the group consisting of transient ischaemic attack, stroke, angina, myocardial infarction, cardiac failure, and peripheral vascular disease.

3. The method of claim 1, wherein said HDL is selected from the group consisting of mature HDL, nascent HDL, reconstituted HDL, HDL produced with recombinant apolipoprotein, and functional peptide and other analogues thereof.

4. The method of claim 3, wherein said HDL is reconstituted HDL.

5. The method of claim 1, wherein said HDL is administered is parenterally.

6. The method of claim 5, wherein said parenteral administration is selected from the group consisting of intravenous, intraarterial, intramuscular and subcutaneous injection or infusion.

7. The method of claim 6, wherein said parenteral administration is intravenous injection or infusion.

8. The method of claim 1, wherein improved endothelial function persists for at least 7 days following HDL administration.

9. A method for the treatment of endothelial dysfunction in a Type 2 diabetic patient, which comprises administering to a Type 2 diabetic patient suffering from endothelial dysfunction associated with a diabetes-induced macrovascular disorder, an amount of high density lipoprotein (HDL) effective to improve endothelial function, wherein said HDL is administered in a dosage range of from 10-80 mg per kg body weight of the patient per treatment, wherein each treatment is separated by at least 7 days.

10. The method of claim 9, wherein said diabetes induced macrovascular disorder is selected from the group consisting of transient ischaemic attack, stroke, angina, myocardial infarction, cardiac failure, and peripheral vascular disease.

11. The method of claim 9, wherein said HDL is selected from the group consisting of mature HDL, nascent HDL, reconstituted HDL, HDL produced with recombinant apolipoprotein, and functional peptide and other analogues thereof.

12. The method of claim 11, wherein said HDL is reconstituted HDL.

13. The method of claim 9, wherein said HDL is administered is parenterally.

14. The method of claim 13, wherein said parenteral administration is selected from the group consisting of intravenous, intraarterial, intramuscular and subcutaneous injection or infusion.

15. The method of claim 14, wherein said parenteral administration is intravenous injection or infusion.

16. The method of claim 9, wherein improved endothelial function persists for at least 7 days following HDL administration.

* * * * *